(12) United States Patent
Kaylor et al.

(10) Patent No.: US 8,367,013 B2
(45) Date of Patent: *Feb. 5, 2013

(54) READING DEVICE, METHOD, AND SYSTEM FOR CONDUCTING LATERAL FLOW ASSAYS

(75) Inventors: Rosann Kaylor, Cumming, GA (US); Difei Yang, Alpharetta, GA (US); Michael Knotts, Roswell, GA (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 1966 days.

This patent is subject to a terminal disclaimer.

(21) Appl. No.: 10/035,013

(22) Filed: Dec. 24, 2001

(65) Prior Publication Data

US 2003/0119202 A1    Jun. 26, 2003

(51) Int. Cl.
*G01N 33/48* (2006.01)
(52) U.S. Cl. .................. 422/403; 422/400; 422/401
(58) Field of Classification Search .................. 422/58, 422/61, 400–403; 436/164, 166, 169, 174
See application file for complete search history.

(56) References Cited

U.S. PATENT DOCUMENTS

| | | |
|---|---|---|
| 164,659 A | 5/1875 | Reckhow et al. |
| 4,094,647 A | 6/1978 | Deutsch et al. |
| 4,110,529 A | 8/1978 | Stoy |
| 4,168,146 A | 9/1979 | Grubb et al. |
| RE30,267 E | 5/1980 | Bruschi |
| 4,210,723 A | 7/1980 | Dorman et al. |
| 4,235,601 A | 11/1980 | Deutsch et al. |
| 4,275,149 A | 6/1981 | Litman et al. |
| 4,312,228 A | 1/1982 | Wohltjen |
| 4,361,537 A | 11/1982 | Deutsch et al. |
| 4,363,874 A | 12/1982 | Greenquist |
| 4,366,241 A | 12/1982 | Tom et al. |
| 4,374,925 A | 2/1983 | Litman et al. |
| 4,385,126 A | 5/1983 | Chen et al. |
| 4,426,451 A | 1/1984 | Columbus |
| 4,427,836 A | 1/1984 | Kowalski et al. |
| 4,435,504 A | 3/1984 | Zuk et al. |

(Continued)

FOREIGN PATENT DOCUMENTS

| | | |
|---|---|---|
| EA | 0308770 B1 | 2/1994 |
| EP | 0073593 A1 | 3/1983 |

(Continued)

OTHER PUBLICATIONS

PCT Search Report for PCT/US02/37653, Apr. 7, 2004.

(Continued)

*Primary Examiner* — Lyle Alexander
(74) *Attorney, Agent, or Firm* — Dority & Manning, P.A.

(57) ABSTRACT

An optical reflectance kit including a reading device and membrane test strip is disclosed for conducting a lateral flow assay. The reading device is portable. Assays may be conducted on bodily fluids to detect with high sensitivity the presence of certain hormones, glucose, or other bodily fluids of interest. Membrane test strips may receive a test fluid or test sample containing an analyte to be detected. The membrane test strips may be inserted directly into a receiving port of a reading device. Shielding stray light from the receiving port improves sensitivity and reduces the entry of stray or ambient light into the reading device. The reading device also includes one or more sensors capable of detecting the intensity of reflected electromagnetic radiation.

16 Claims, 9 Drawing Sheets

U.S. PATENT DOCUMENTS

| | | | |
|---|---|---|---|
| 4,441,373 A | 4/1984 | White | |
| 4,442,204 A | 4/1984 | Greenquist et al. | |
| 4,444,592 A | 4/1984 | Ludwig | |
| 4,477,635 A | 10/1984 | Mitra | |
| 4,480,042 A | 10/1984 | Craig et al. | |
| 4,533,499 A | 8/1985 | Clark et al. | |
| 4,533,629 A | 8/1985 | Litman et al. | |
| 4,534,356 A | 8/1985 | Papadakis | |
| 4,537,861 A | 8/1985 | Elings et al. | |
| 4,540,659 A | 9/1985 | Litman et al. | |
| 4,552,458 A | 11/1985 | Lowne | |
| 4,561,286 A | 12/1985 | Sekler et al. | |
| 4,562,157 A | 12/1985 | Lowe et al. | |
| 4,595,661 A | 6/1986 | Cragle et al. | |
| 4,596,697 A | 6/1986 | Ballato | |
| 4,614,723 A | 9/1986 | Schmidt et al. | |
| 4,632,559 A | 12/1986 | Brunsting | |
| 4,661,235 A | 4/1987 | Krull et al. | |
| 4,698,262 A | 10/1987 | Schwartz et al. | |
| 4,703,017 A | 10/1987 | Campbell et al. | |
| 4,722,889 A | 2/1988 | Lee et al. | |
| 4,727,019 A | 2/1988 | Valkirs et al. | |
| 4,731,337 A | 3/1988 | Luotola et al. | |
| 4,743,542 A | 5/1988 | Graham, Jr. et al. | |
| 4,776,944 A | 10/1988 | Janata et al. | |
| 4,833,088 A | 5/1989 | DeSimone et al. | |
| 4,837,168 A | 6/1989 | de Jaeger et al. | |
| 4,842,783 A | 6/1989 | Blaylock | |
| 4,843,000 A | 6/1989 | Litman et al. | |
| 4,843,021 A | 6/1989 | Noguchi et al. | |
| 4,844,613 A | 7/1989 | Batchelder et al. | |
| 4,849,338 A | 7/1989 | Litman et al. | |
| 4,855,240 A | 8/1989 | Rosenstein et al. | |
| 4,857,453 A | 8/1989 | Ullman et al. | |
| 4,871,258 A | 10/1989 | Herpichboehm et al. | |
| 4,877,586 A | 10/1989 | Devaney, Jr. et al. | |
| 4,877,747 A | 10/1989 | Stewart | |
| 4,895,017 A | 1/1990 | Pyke et al. | |
| 4,916,056 A | 4/1990 | Brown, III et al. | |
| 4,917,503 A | 4/1990 | Bhattacharjee | |
| 4,940,734 A | 7/1990 | Ley et al. | |
| 4,963,498 A | 10/1990 | Hillman et al. | |
| 4,973,670 A | 11/1990 | McDonald et al. | |
| 4,992,385 A | 2/1991 | Godfrey | |
| 5,003,178 A | 3/1991 | Livesay | |
| 5,023,053 A | 6/1991 | Finlan | |
| 5,026,653 A | 6/1991 | Lee et al. | |
| 5,035,863 A | 7/1991 | Finlan et al. | |
| 5,055,265 A | 10/1991 | Finlan | |
| 5,063,081 A | 11/1991 | Cozzette et al. | |
| 5,064,619 A | 11/1991 | Finlan | |
| 5,075,077 A | 12/1991 | Durley, III et al. | |
| 5,076,094 A | 12/1991 | Frye et al. | |
| 5,096,671 A | 3/1992 | Kane et al. | |
| 5,114,676 A | 5/1992 | Leiner et al. | |
| 5,120,662 A | 6/1992 | Chan et al. | |
| 5,124,254 A | 6/1992 | Hewlins et al. | |
| 5,134,057 A | 7/1992 | Kuypers et al. | |
| 5,137,609 A | 8/1992 | Manian et al. | |
| 5,143,854 A | 9/1992 | Pirrung et al. | |
| 5,145,784 A | 9/1992 | Cox et al. | |
| 5,152,758 A | 10/1992 | Kaetsu et al. | |
| 5,156,953 A | 10/1992 | Litman et al. | |
| 5,182,135 A | 1/1993 | Giesecke et al. | |
| 5,196,350 A | 3/1993 | Backman et al. | |
| 5,200,084 A | 4/1993 | Liberti et al. | |
| 5,221,454 A | 6/1993 | Manian et al. | |
| 5,225,935 A | 7/1993 | Watanabe et al. | |
| 5,234,813 A | 8/1993 | McGeehan et al. | |
| 5,235,238 A | 8/1993 | Nomura et al. | |
| 5,238,815 A | 8/1993 | Higo et al. | |
| 5,242,828 A | 9/1993 | Bergström et al. | |
| 5,252,459 A | 10/1993 | Tarcha et al. | |
| 5,262,299 A | 11/1993 | Evangelista et al. | |
| 5,268,306 A | 12/1993 | Berger et al. | |
| 5,304,468 A * | 4/1994 | Phillips et al. | 435/14 |
| 5,314,923 A | 5/1994 | Cooke et al. | |
| 5,316,727 A | 5/1994 | Suzuki et al. | |
| 5,320,944 A | 6/1994 | Okada et al. | |
| 5,321,492 A | 6/1994 | Detwiler et al. | |
| 5,327,225 A | 7/1994 | Bender et al. | |
| 5,330,898 A | 7/1994 | Bar-Or et al. | |
| 5,342,759 A | 8/1994 | Litman et al. | |
| 5,352,582 A | 10/1994 | Lichtenwalter et al. | |
| 5,356,782 A | 10/1994 | Moorman et al. | |
| 5,358,852 A | 10/1994 | Wu | |
| 5,369,717 A | 11/1994 | Attridge | |
| 5,374,563 A | 12/1994 | Maule | |
| 5,376,255 A | 12/1994 | Gumbrecht et al. | |
| 5,387,503 A | 2/1995 | Selmer et al. | |
| 5,395,754 A | 3/1995 | Lambotte et al. | |
| 5,415,842 A | 5/1995 | Maule | |
| 5,418,136 A | 5/1995 | Miller et al. | |
| 5,424,219 A | 6/1995 | Jirikowski | |
| 5,432,057 A | 7/1995 | Litman et al. | |
| 5,436,161 A | 7/1995 | Bergström et al. | |
| 5,445,971 A | 8/1995 | Rohr | |
| 5,451,683 A | 9/1995 | Barrett et al. | |
| 5,455,475 A | 10/1995 | Josse et al. | |
| 5,464,741 A | 11/1995 | Hendrix | |
| 5,466,574 A | 11/1995 | Liberti et al. | |
| 5,467,778 A | 11/1995 | Catt et al. | |
| 5,468,606 A | 11/1995 | Bogart et al. | |
| 5,482,830 A | 1/1996 | Bogart et al. | |
| 5,482,867 A | 1/1996 | Barrett et al. | |
| 5,484,867 A | 1/1996 | Lichtenhan et al. | |
| 5,489,678 A | 2/1996 | Fodor et al. | |
| 5,489,988 A | 2/1996 | Ackley et al. | |
| 5,492,840 A | 2/1996 | Malmqvist et al. | |
| 5,500,350 A | 3/1996 | Baker et al. | |
| 5,504,013 A | 4/1996 | Senior | |
| 5,508,171 A | 4/1996 | Walling et al. | |
| 5,510,481 A | 4/1996 | Bednarski et al. | |
| 5,512,131 A | 4/1996 | Kumar et al. | |
| 5,514,559 A | 5/1996 | Markert-Hahn et al. | |
| 5,514,785 A | 5/1996 | Van Ness et al. | |
| 5,516,635 A | 5/1996 | Ekins et al. | |
| 5,518,689 A | 5/1996 | Dosmann et al. | |
| 5,518,883 A | 5/1996 | Soini | |
| 5,527,711 A | 6/1996 | Tom-Moy et al. | |
| 5,534,132 A | 7/1996 | Vreeke et al. | |
| 5,554,541 A | 9/1996 | Malmqvist et al. | |
| 5,569,608 A | 10/1996 | Sommer | |
| 5,571,684 A | 11/1996 | Lawrence et al. | |
| 5,573,909 A | 11/1996 | Singer et al. | |
| 5,585,279 A | 12/1996 | Davidson | |
| 5,589,401 A | 12/1996 | Hansen et al. | |
| 5,591,581 A | 1/1997 | Massey et al. | |
| 5,596,414 A | 1/1997 | Tyler | |
| 5,599,668 A | 2/1997 | Stimpson et al. | |
| 5,618,888 A | 4/1997 | Choi et al. | |
| 5,620,850 A | 4/1997 | Bamdad et al. | |
| 5,637,509 A | 6/1997 | Hemmilä et al. | |
| 5,647,994 A | 7/1997 | Tuunanen et al. | |
| 5,658,443 A | 8/1997 | Yamamoto et al. | |
| 5,663,213 A | 9/1997 | Jones et al. | |
| 5,670,381 A | 9/1997 | Jou et al. | |
| 5,672,256 A | 9/1997 | Yee | |
| 5,700,636 A | 12/1997 | Sheiness et al. | |
| 5,726,064 A | 3/1998 | Robinson et al. | |
| 5,731,147 A | 3/1998 | Bard et al. | |
| 5,736,188 A | 4/1998 | Alcock et al. | |
| 5,753,517 A | 5/1998 | Brooks et al. | |
| 5,770,416 A | 6/1998 | Lihme et al. | |
| 5,780,308 A | 7/1998 | Ching et al. | |
| 5,795,470 A | 8/1998 | Wang et al. | |
| 5,795,543 A | 8/1998 | Poto et al. | |
| 5,811,526 A | 9/1998 | Davidson | |
| 5,827,748 A | 10/1998 | Golden | |
| 5,834,226 A | 11/1998 | Maupin | |
| 5,837,429 A | 11/1998 | Nohr et al. | |
| 5,837,546 A * | 11/1998 | Allen et al. | 436/169 |
| 5,843,692 A | 12/1998 | Phillips et al. | |
| 5,852,229 A | 12/1998 | Josse et al. | |
| 5,876,944 A | 3/1999 | Kuo | |
| 5,885,527 A | 3/1999 | Buechler | |
| 5,906,921 A | 5/1999 | Ikeda et al. | |

| | | |
|---|---|---|
| 5,910,447 A | 6/1999 | Lawrence et al. |
| 5,910,940 A | 6/1999 | Guerra |
| 5,922,537 A | 7/1999 | Ewart et al. |
| 5,922,550 A | 7/1999 | Everhart et al. |
| 5,951,492 A | 9/1999 | Douglas et al. |
| 5,962,995 A | 10/1999 | Avnery |
| 6,004,530 A | 12/1999 | Sagner et al. |
| 6,020,047 A | 2/2000 | Everhart |
| 6,027,904 A | 2/2000 | Devine et al. |
| 6,027,944 A | 2/2000 | Robinson et al. |
| 6,030,792 A | 2/2000 | Otterness et al. |
| 6,030,840 A | 2/2000 | Mullinax et al. |
| 6,033,574 A | 3/2000 | Siddiqi |
| 6,048,623 A | 4/2000 | Everhart et al. |
| 6,060,256 A | 5/2000 | Everhart et al. |
| 6,080,391 A | 6/2000 | Tsuchiya et al. |
| 6,084,683 A | 7/2000 | Bruno et al. |
| 6,087,184 A | 7/2000 | Magginetti et al. |
| 6,099,484 A | 8/2000 | Douglas et al. |
| 6,103,537 A | 8/2000 | Ullman et al. |
| 6,117,090 A | 9/2000 | Caillouette |
| 6,136,549 A | 10/2000 | Feistel |
| 6,136,611 A | 10/2000 | Saaski et al. |
| 6,139,961 A | 10/2000 | Blankenship et al. |
| 6,151,110 A | 11/2000 | Markart |
| 6,165,798 A | 12/2000 | Brooks |
| 6,171,780 B1 | 1/2001 | Pham et al. |
| 6,171,870 B1 | 1/2001 | Freitag |
| 6,174,646 B1 | 1/2001 | Hirai et al. |
| 6,177,281 B1 | 1/2001 | Manita |
| 6,180,288 B1 | 1/2001 | Everhart et al. |
| 6,183,972 B1 | 2/2001 | Kuo et al. |
| 6,184,042 B1 | 2/2001 | Neumann et al. |
| 6,194,220 B1 | 2/2001 | Malick et al. |
| 6,200,820 B1 | 3/2001 | Hansen et al. |
| 6,221,238 B1 | 4/2001 | Grundig et al. |
| 6,221,579 B1 | 4/2001 | Everhart et al. |
| 6,234,974 B1 | 5/2001 | Catt et al. |
| 6,235,241 B1 | 5/2001 | Catt et al. |
| 6,235,471 B1 | 5/2001 | Knapp et al. |
| 6,235,491 B1 | 5/2001 | Connolly |
| 6,241,863 B1 | 6/2001 | Monbouquette |
| 6,242,268 B1 | 6/2001 | Wieder et al. |
| 6,255,066 B1 | 7/2001 | Louderback |
| 6,261,779 B1 | 7/2001 | Barbera-Guillem et al. |
| 6,268,162 B1 | 7/2001 | Phillips et al. |
| 6,268,222 B1 | 7/2001 | Chandler et al. |
| 6,270,637 B1 | 8/2001 | Crismore et al. |
| 6,271,040 B1 | 8/2001 | Buechler |
| 6,274,326 B1 | 8/2001 | Stoughton |
| 6,281,006 B1 | 8/2001 | Heller et al. |
| 6,284,472 B1 | 9/2001 | Wei et al. |
| 6,287,783 B1 | 9/2001 | Maynard et al. |
| 6,287,871 B1 | 9/2001 | Herron et al. |
| 6,294,392 B1 | 9/2001 | Kuhr et al. |
| 6,306,665 B1 | 10/2001 | Buck et al. |
| D450,854 S | 11/2001 | Lipman et al. |
| 6,331,438 B1 | 12/2001 | Aylott et al. |
| 6,335,203 B1 | 1/2002 | Patel et al. |
| 6,348,186 B1 | 2/2002 | Sutton et al. |
| 6,362,011 B1 | 3/2002 | Massey et al. |
| 6,368,873 B1 | 4/2002 | Chang et al. |
| 6,368,875 B1 | 4/2002 | Geisberg |
| 6,387,707 B1 | 5/2002 | Seul et al. |
| 6,391,558 B1 | 5/2002 | Henkens et al. |
| 6,399,295 B1 | 6/2002 | Kaylor et al. |
| 6,399,397 B1 | 6/2002 | Zarling et al. |
| 6,407,492 B1 | 6/2002 | Avnery et al. |
| 6,411,439 B2 | 6/2002 | Nishikawa |
| 6,413,410 B1 | 7/2002 | Hodges et al. |
| 6,436,651 B1 | 8/2002 | Everhart et al. |
| 6,436,722 B1 | 8/2002 | Clark et al. |
| 6,444,423 B1 | 9/2002 | Meade et al. |
| 6,448,091 B1 | 9/2002 | Massey et al. |
| 6,451,607 B1 | 9/2002 | Lawrence et al. |
| 6,455,861 B1 | 9/2002 | Hoyt |
| 6,461,496 B1 | 10/2002 | Feldman et al. |
| 6,468,741 B1 | 10/2002 | Massey et al. |
| 6,472,226 B1 | 10/2002 | Barradine et al. |
| 6,479,146 B1 | 11/2002 | Caruso et al. |
| 6,509,085 B1 | 1/2003 | Kennedy |
| 6,511,814 B1 | 1/2003 | Carpenter |
| 6,556,299 B1 | 4/2003 | Rushbrooke et al. |
| 6,566,508 B2 | 5/2003 | Bentsen et al. |
| 6,573,040 B2 | 6/2003 | Everhart et al. |
| 6,579,673 B2 | 6/2003 | McGrath et al. |
| 6,582,930 B1 | 6/2003 | Ponomarev et al. |
| 6,585,939 B1 | 7/2003 | Dapprich |
| 6,613,583 B1 | 9/2003 | Richter et al. |
| 6,617,488 B1 | 9/2003 | Springer et al. |
| 6,670,115 B1 | 12/2003 | Zhang |
| 6,720,007 B2 | 4/2004 | Walt et al. |
| 6,787,368 B1 | 9/2004 | Wong et al. |
| 6,815,218 B1 | 11/2004 | Jacobson et al. |
| 6,867,051 B1 * | 3/2005 | Anderson et al. .............. 436/518 |
| 2002/0164659 A1 | 11/2002 | Rao et al. |
| 2003/0178309 A1 | 9/2003 | Huang et al. |
| 2004/0014073 A1 | 1/2004 | Trau et al. |

FOREIGN PATENT DOCUMENTS

| | | | |
|---|---|---|---|
| EP | 0617285 | A2 | 9/1994 |
| EP | 0617285 | A3 | 9/1994 |
| WO | 0078917 | A1 | 12/2000 |
| WO | 0150129 | A3 | 7/2001 |
| WO | 0151029 | A2 | 7/2001 |
| WO | 02077646 | A1 | 10/2002 |
| WO | 03058246 | A1 | 7/2003 |

OTHER PUBLICATIONS

PCT Search Report for PCT/US03/34543, Apr. 6, 2004.
PCT Search Report for PCT/US03/34544, Apr. 20, 2004.
Article—*New Use of Cyanosilane Coupling Agent for Direct Binding of Antibodies to Silica Supports. Physicochemical Characterization of Molecularly Bioengineered Layers*, Sandrine Falipou, Jean-Marc Chovelon, Claude Martelet, Jacqueline Margonari and Dominique Cathignol, Bioconjugate Chem., vol. 10, No. 3, 1999, pp. 346-353.
PCT Search Report and Written Opinion for PCT/US2004/006412 Sep. 28, 2004.
PCT Search Report and Written Opinion for PCT/US2004/006414 Sep. 28, 2004.

* cited by examiner

READING DEVICE, METHOD, AND SYSTEM FOR CONDUCTING LATERAL FLOW ASSAYS

BACKGROUND OF THE INVENTION

Membrane-based test devices, particularly devices used in diagnostic medicine, employ a variety of internal and external calibrators to provide a qualitative or a quantitative result for an analyte of interest in a test solution. One type of membrane-based test device is a lateral flow assay.

In general, lateral flow assays are membrane-based test devices in which a sample that is suspected of containing the analyte of interest is placed at or near one end of a membrane strip. The sample is carried to the opposite end of the membrane strip by a liquid phase that traverses the membrane strip by capillary action. While traversing the membrane strip, the analyte in the test sample, if any, encounters one or more "capture" reagents with which it may react to produce a detectable signal.

Home use assay devices such as pregnancy tests and the like are now well established. Home use assays may be intended to detect physiological changes in the human body, with the objective of promoting the health and well being of an individual. Consumers are becoming increasingly health conscious, and it is a significant advantage if the consumer is capable of monitoring his or her own bodily functions, including levels of hormones and the like.

There are many different assays that are indicative of physiological changes in the human body. Furthermore, there are many different assay devices that operate by reading an assay strip or test sample. Some devices use fluorescence emission, and others use light reflectance.

U.S. Pat. No. 6,235,241 B1 to Catt et al. ("the Catt patent") is directed to an assay result reader used in conjunction with an assay device. A commercially available device similar to that shown in the Catt patent is known as a UNIPATH CLEAR PLAN Easy® Fertility Monitor. This device is shown in FIG. 1 herein, and comprises a fertility monitoring device 21 with a removable hand held cover 22, which fits into a receiver 23 upon the housing 25. Bodily fluids are applied to the test strip 24, and the test strip 24 may be placed into the receiver 23, where the test strip 24 receives light that shines through a window 26 upon the test strip 24. Then, the level of reflected light is analyzed to give a result.

One of the problems with fertility monitoring devices as described is that they are not capable of providing a high degree of sensitivity, in many instances. That is, some analytes need to be monitored for medical purposes, but do not require a high degree of sensitivity or a sophisticated instrument to detect accurately and precisely the levels of analyte. Many currently available home use reading devices have a low signal to noise ratio, which may be caused in part by the undesirable introduction of excess amounts of stray or ambient light into the viewing window. In conducting precise measurements using a reflectance-based regime, it is critical that the amount of stray ambient light be reduced or eliminated to achieve a high degree of sensitivity. It is therefore highly desirable to maximize the signal to noise ratio, and increase the sensitivity of such reading devices.

Another reading device for home use is known as an ACCUCHECK® Blood Glucose Meter manufactured and distributed by Boehringer Mannheim Diagnostics of Indianapolis, Ind. 46250. The ACCUCHECK® device is a reflectance-based instrument designed for home use in checking blood glucose levels. The instrument does not employ a lateral flow assay. Instead, a user is instructed to place a drop of blood upon a test pad. The reflectance sensor portion of the instrument contains a removable holder, with two rectangular windows.

What is needed in the industry is a sensitive reading device designed for lateral flow assay test strips. A reading device that provides an efficient and reliable means for quickly placing a test strip into position to receive a reading or result, while avoiding excess ambient and stray light would be desirable. A reading device providing high sensitivity for detecting hormones and the like would be desirable. A reading device having a window that achieves a high degree of efficiency in the transmission and reflectance of light would be useful.

SUMMARY OF THE INVENTION

In the invention, a reading device for lateral flow assays, and a system for conducting assays, may be provided. The reading device is configured for detecting an assay result from a membrane strip, in which the result is revealed by the binding of a detectable analyte within a detection zone along the membrane strip. The assay reading device comprises a housing and a receiving port within the housing. The receiving port may include a light barrier structure, and admits a membrane strip directly from the outside of the housing. That is, a membrane strip is inserted into the receiving port. The receiving port may be configured for minimizing the introduction of stray or ambient light into the reading device.

A reading mechanism also may be provided which includes a source of electromagnetic radiation, and one or more sensors capable of detecting the intensity of reflected electromagnetic radiation. The source of radiation and the sensors may be positioned within the reading mechanism so that when the membrane strip is admitted into the receiving port, the radiation impacts the detection zone upon the membrane strip prior to impacting the sensor.

In another embodiment of the invention, a test kit, including a lateral flow assay reading device and a porous liquid permeable membrane strip may be provided.

In yet another embodiment of the invention, a system for conducting a lateral flow assays may be provided for detecting the quantity of analyte that resides in a test liquid. The system may include a probe configured for generating a detectable signal, and a membrane strip designed for mobilizing a test liquid. The membrane strip includes a detection zone. Furthermore, a reading device as previously described is employed, with a receiving port and light barrier structure configured for minimizing stray light into the reader. An assay result having increased sensitivity is achieved by way of the invention.

BRIEF DESCRIPTION OF THE DRAWINGS

A full and enabling disclosure of this invention, including the best mode shown to one of ordinary skill in the art, is set forth in this specification. The following Figures illustrate the invention:

FIG. 5b shows a design layout for the electronics of the reading device, including a microcontroller, LCD display, and the like;

DETAILED DESCRIPTION OF THE INVENTION

Reference now will be made to the embodiments of the invention, one or more examples of which are set forth below. Each example is provided by way of explanation of the invention, not as a limitation of the invention. In fact, it will be apparent to those skilled in the art that various modifications and variations can be made in this invention without departing from the scope or spirit of the invention. For instance, features illustrated or described as part of one embodiment can be used on another embodiment to yield a still further embodiment. Thus, it is intended that the present invention cover such modifications and variations as come within the scope of the appended claims and their equivalents.

In the invention, an optical reflectance meter or reading device is provided. The reading device may be used with lateral flow assays to provide quantitative results. The metering device may be designed to provide improved sensitivity and increased accuracy. The method and system of the invention may serve as a more accurate and sensitive alternative to direct visual examination of a membrane assay strip.

The reading device of the invention may include various components including a light source such as a light emitting diode ("LED") or laser, a light beam modulator, mirror, lenses, photo diodes, sample holders and other optional components, as further described herein. In any event, the sample holder provides for easy insertion of membrane test strips, with a minimal amount of pass through of ambient or stray light, thus reducing the noise level. A reading device having an improved signal to noise ratio is provided, with greater sensitivity. The sample holder may include a mechanical design having a spring-loaded member. In some applications, at least two different stop positions are provided for the same membrane test strip wherein the first stop position may be used to provide a reference reading, and a second stop position may be used to read actual samples in a detection area or a detection zone.

Figure 1:
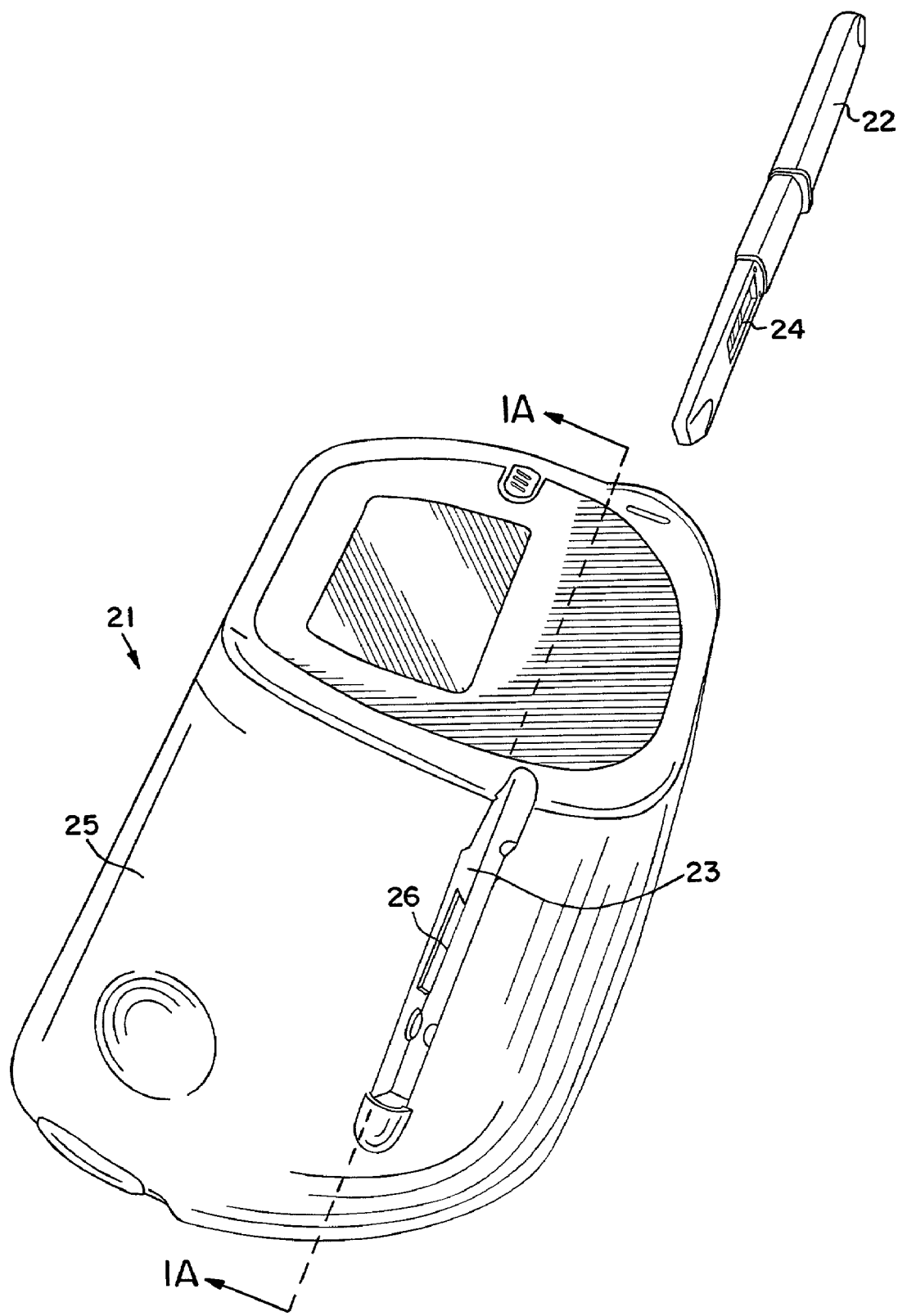
FIG. 1 is a perspective view of the CLEAR PLAN EASY® Fertility Monitor previously discussed.
Figure 2:
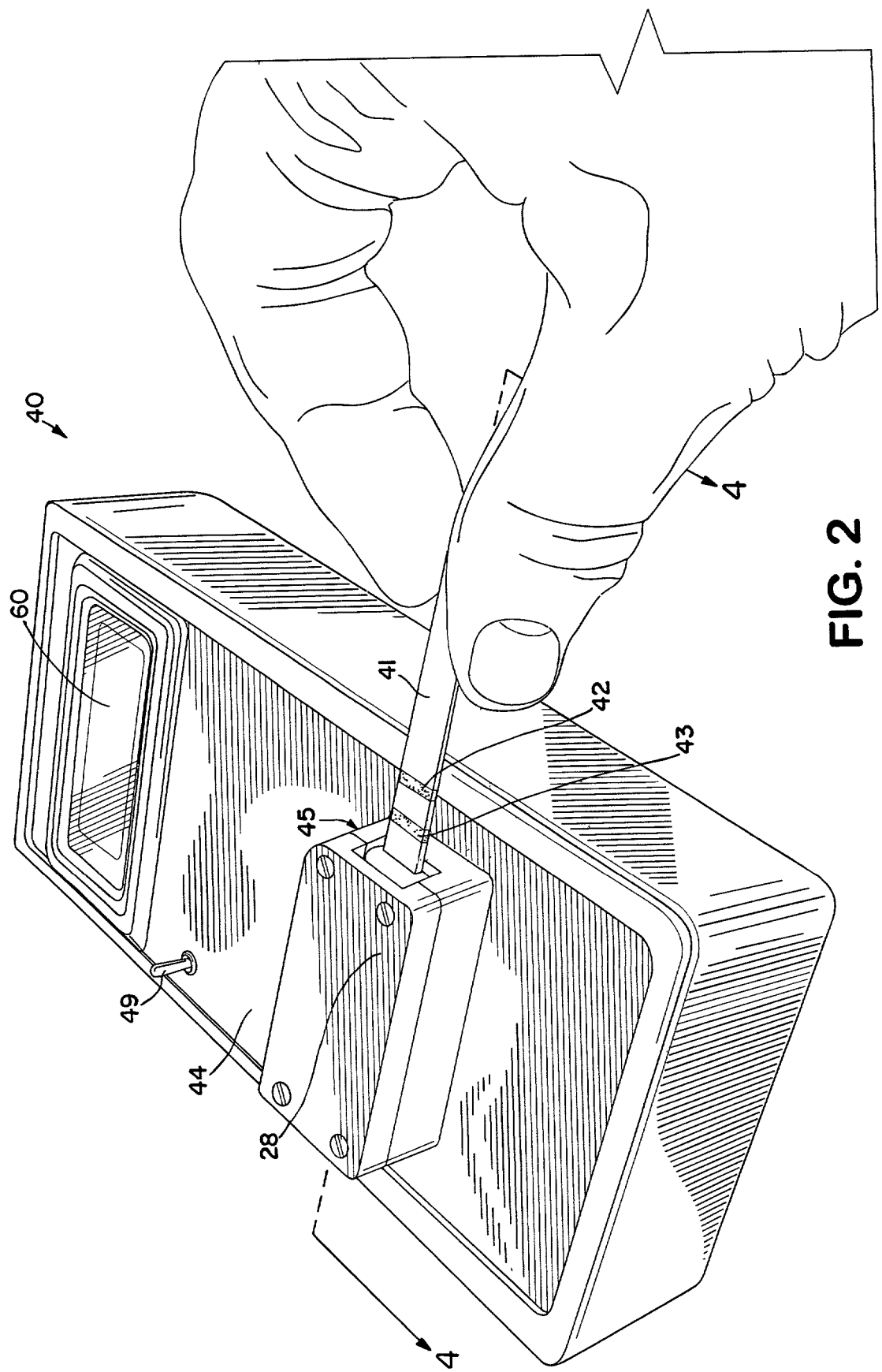
FIG. 2 is a perspective view of one embodiment of the reading device of the invention, showing the light barrier structure and receiving port.

One embodiment of the invention is further illustrated in FIG. 2, wherein a reading device 40 receives a membrane strip 41 into a receiving port 45 to provide a result. A light barrier structure 28 also is shown. A detection zone 42 upon the membrane strip 41 is located some distance from a reference zone 43, which gives a base line reference or calibration reading. In the particular embodiment shown, the detection zone 42 is provided towards the outside, while the reference zone 43 is towards the inside, but it should be recognized that the positions of these respective zones could be reversed from that which is shown in FIG. 2.

The reading device 40 may include a housing exterior 44, and on/off switch 49, and housing interior (not shown in FIG. 2). In FIG. 2, an LCD display 60 is shown.

Figure 3:
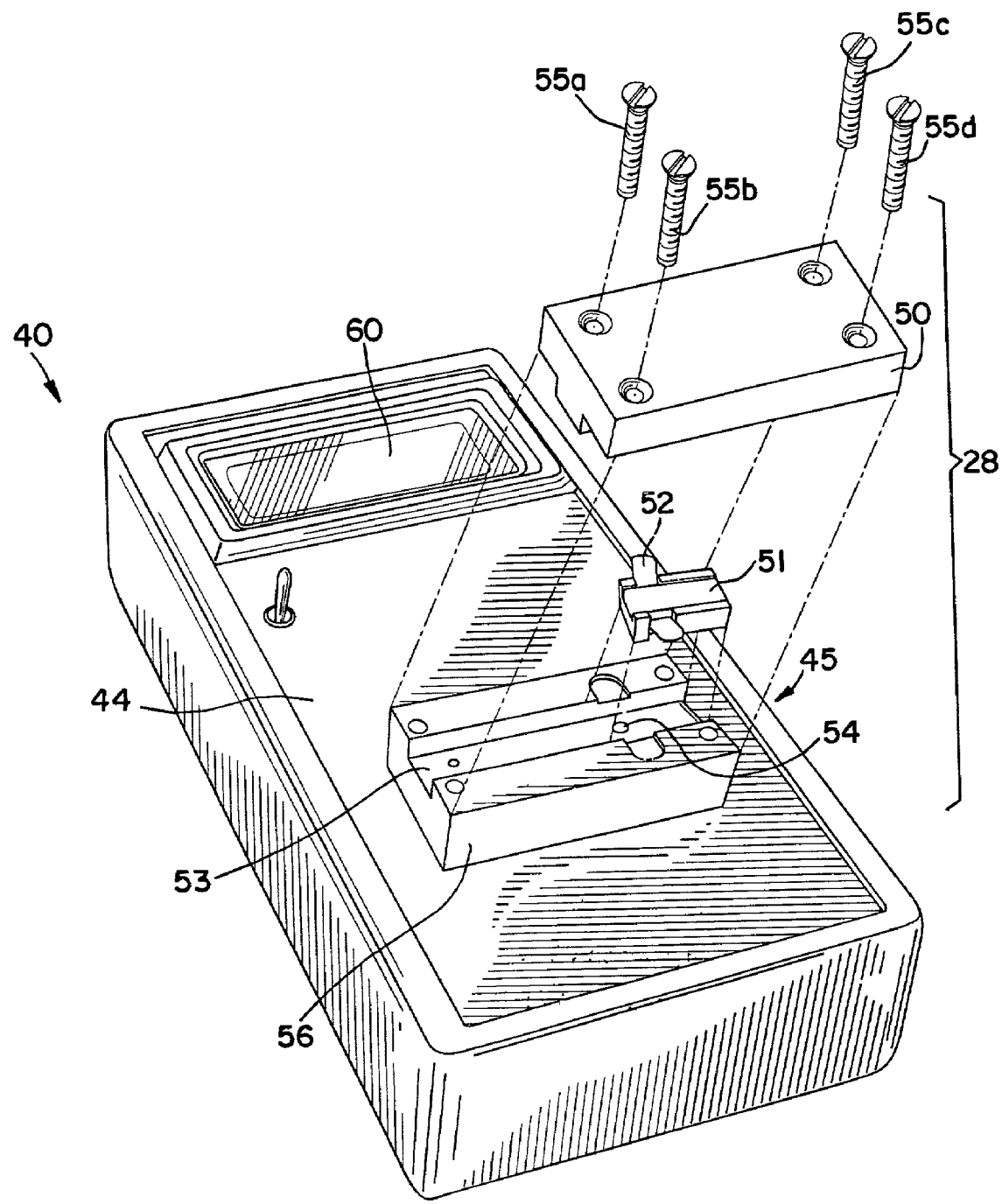
FIG. 3 shows a perspective view of the reading device in which the receiving port 45 has been exploded upwards to reveal details.

In FIG. 3, the light barrier structure 28 is shown in a view with the components exploded upwards from the housing exterior 44 of the reading device 40. The top plate 50 is also shown. The device shown in FIG. 3 corresponds to the device shown in FIG. 2, and is essentially the same embodiment. The receiving port 45 is bounded on its lower edge by bottom plate 56, and on its upper edge by top plate 50. Within the receiving port 45 there is a pressure plate 51, under which the membrane strip 41 is inserted. The pressure plate 51 is held by spring 52 in a resilient engagement with the membrane strip 41 (not shown in FIG. 3). The membrane strip 41 is held over a light transmissive region 54, which happens to be a circular aperture in FIG. 3. However, the aperture could be of many different shapes and sizes, and most preferably approximates the size and/or shape of the zone of interest upon the membrane strip 41 that is to be examined. The channel 53 forms the conduit through which the membrane strip 41 is inserted. Screws 55a-d holds the top plate 50 down upon the housing 44.

Figure 3A:
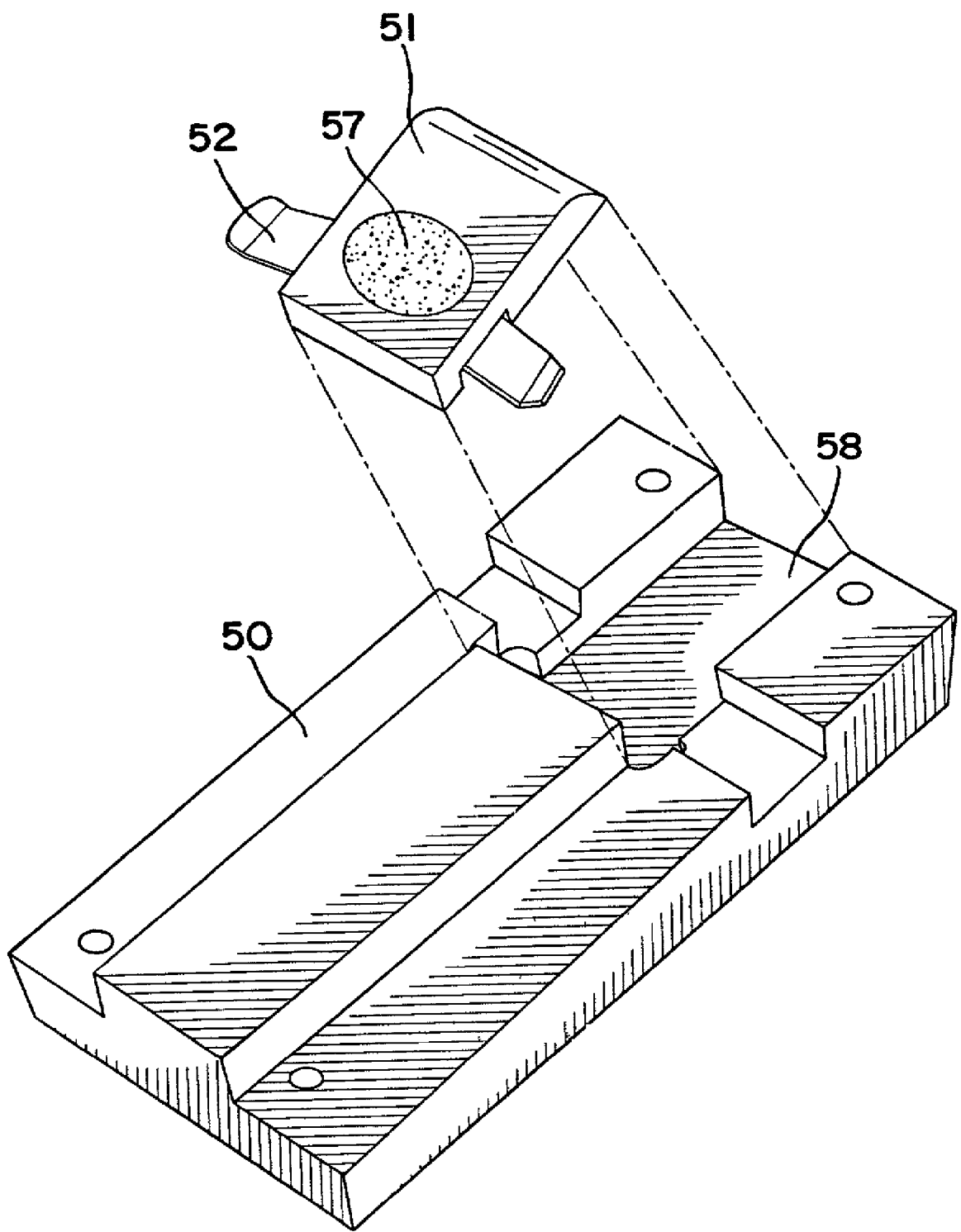
FIG. 3a is a view of the underside of the top plate, showing interaction of the pressure plate with the top plate in the receiving port.

In FIG. 3a, the underside of top plate 50 is shown, revealing a recess 58. Within the recess 58 resides the pressure plate 51, which is held in springing engagement by spring 52. Also shown is a light-absorbing member 57, which rests upon the top or upper surface of membrane strip 41 (see FIG. 2). The light-absorbing member 57 acts as a low reflectance specimen in contact with the aperture 54 that allows the instrument to be calibrated to eliminate the effects of internal reflections within the sensor housing. In practice, such calibration can be performed automatically by the microprocessor when power is first applied to the instrument. Furthermore, the light absorbing member 57 may absorb any light which is transmitted completely through the membrane strip 41, so that such light is not reflected back downward towards the sensor 92 (see FIG. 5a). In this way, the sensitivity and signal to noise ratio of the reading device 40 is maximized.

The light-absorbing member 57 may include almost any type of material that is capable of absorbing light, such as a black or dark colored flocking, plastic, metal, felt, or other material. For example, materials that are used in the photography arts that are known to absorb light could be employed. Such materials may be flexible and/or conformable, and may be comprised of felt. There is no particular size or shape that is preferred for a light-absorbing member 57, but it is important that the light-absorbing member 57 cover completely the area under which the membrane strip 41 is being impacted by light from its underside. One optional feature of the light-absorbing member 57 would be to provide a flexible or conformable form fit to the test strip, by using felt or drapable material.

Figure 4:
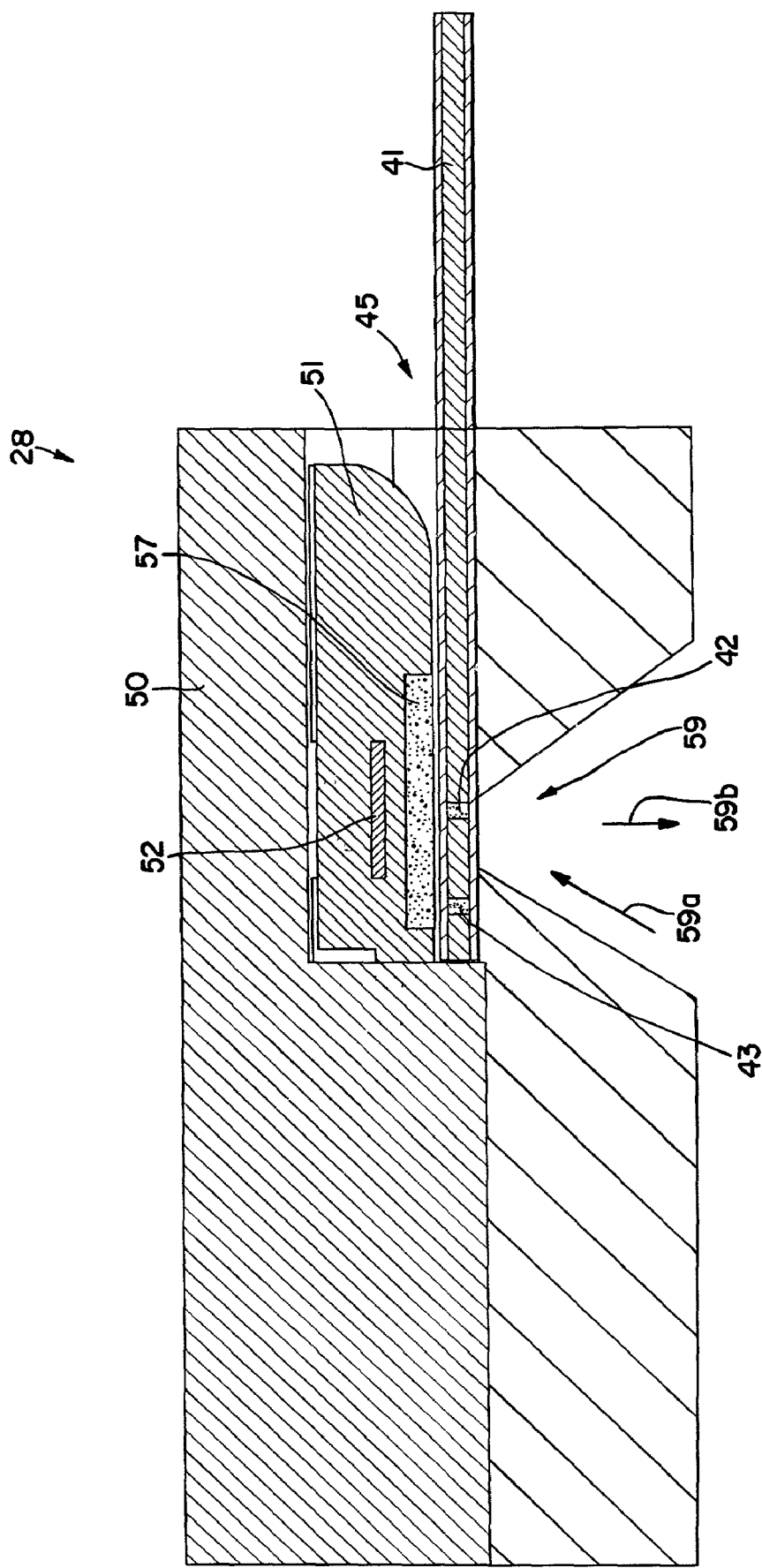
FIG. 4 shows a cross sectional view of the receiving port in one embodiment of the invention, as taken along line 4-4 of FIG. 2.

FIG. 4 shows a cross section of the light barrier structure 28 with receiving port 45 as shown in lines 4-4 of FIG. 2. The receiving port 45 comprises a pressure plate 51 that fits between a top plate 50 and a bottom plate 56. A membrane strip 41 is inserted below the pressure plate 51, where the detection zone 42 of the membrane strip 41 may be placed directly over a light pathway 59. Light generated by a light source (now shown in FIG. 4) such as a light emitting diode (LED) passes upwards along arrow 59a and is reflected downward from membrane strip 41 along arrow 59b as seen in FIG. 4.

Figure 5:
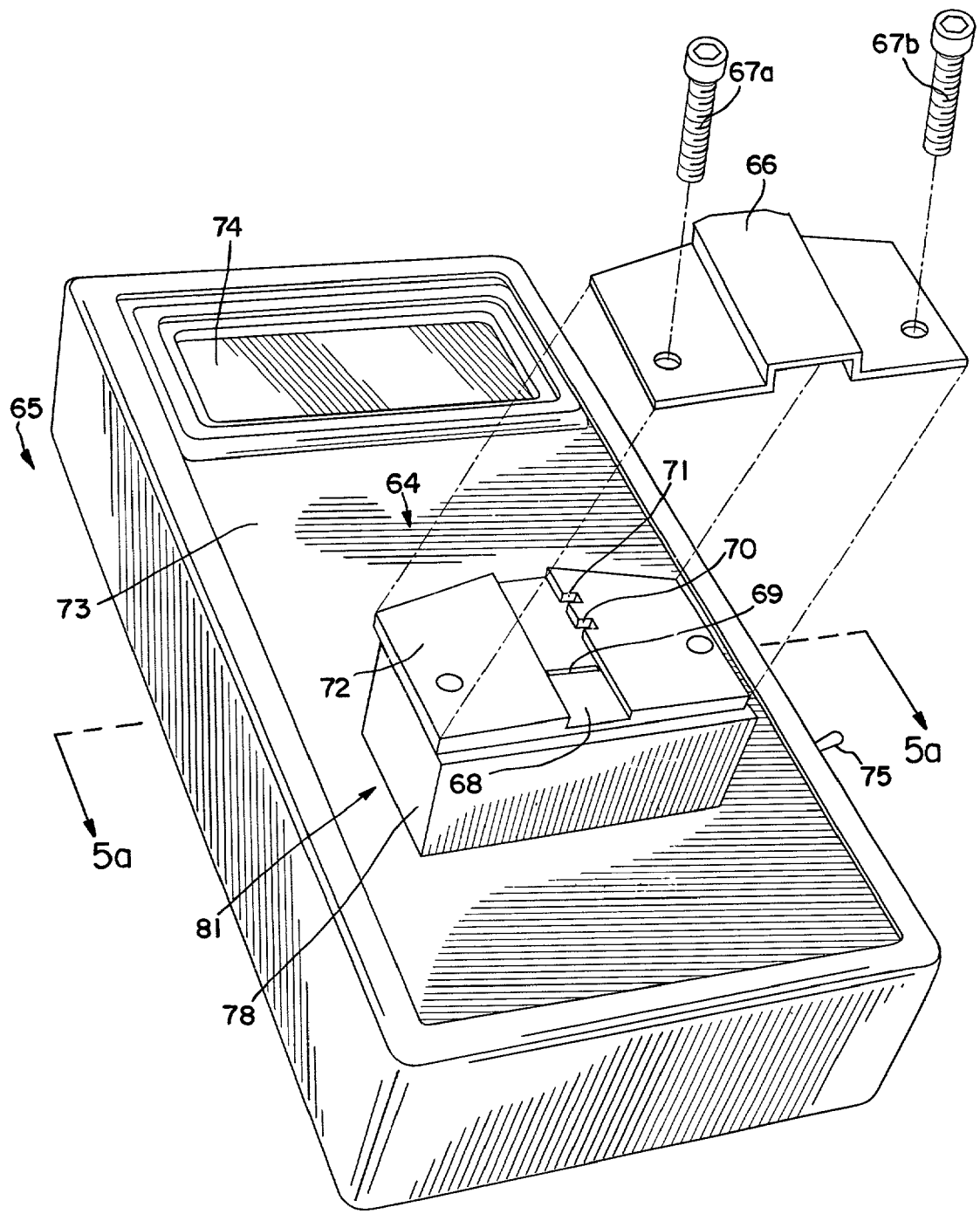
FIG. 5 shows an alternate embodiment of the reading device of the invention having a channel on the upper surface of the reading device configured to receive a membrane test strip.
Figure 5A:
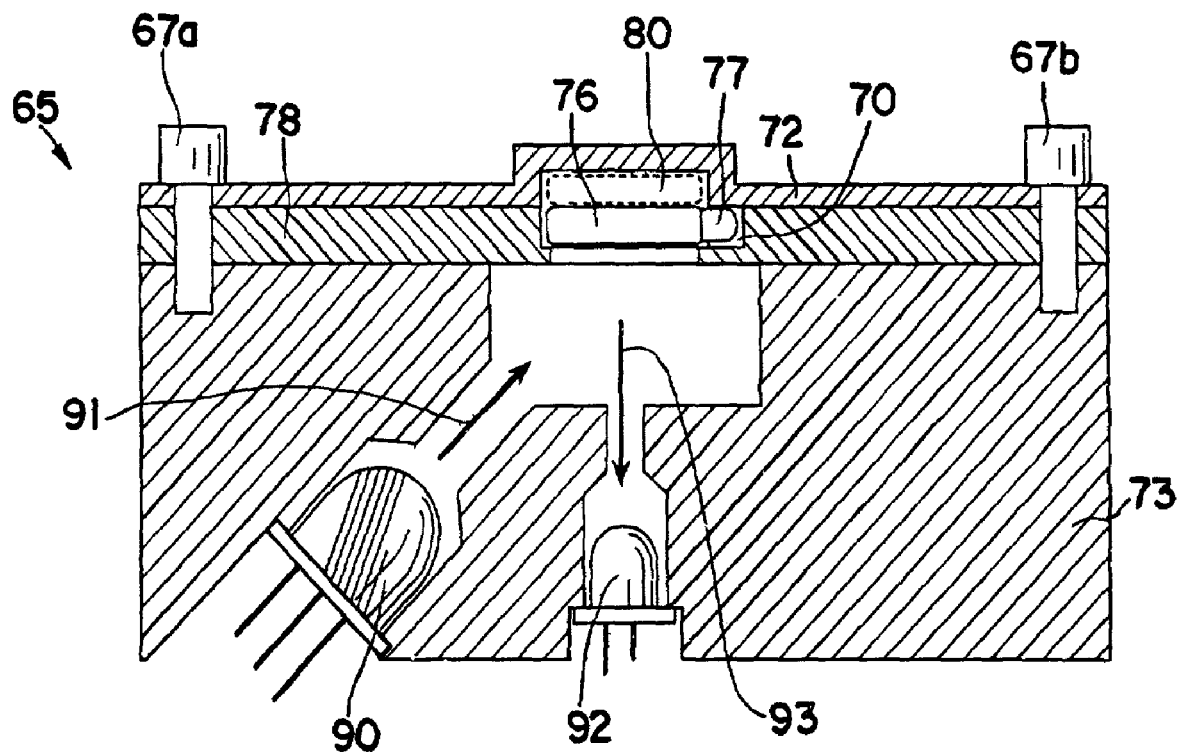
FIG. 5a shows a cross sectional view of the membrane strip receiving portion of the reading device as taken along lines 5a-5a in FIG. 5.

The internal light emitting and sensing components of the reading device shown in FIGS. 2-4 is essentially the same as that shown in FIGS. 5-5a.

It is important to the sensitivity of the reading device 40 that the light aperture located immediately below the membrane strip 41 is of a size that approximates the size of detection zone 42 upon the membrane strip 41. In other applications, the aperture (not shown in FIG. 4) may be slightly larger than the detection zone 42. In some cases, the aperture could be about 1.3 or even 1.8 times larger in area than the detection zone 42. However, it has been found that the closer the aperture corresponds to the size of the detection zone 42 upon the membrane strip 41, the higher the signal to noise ratio that can be achieved by the reading device 40, and the more sensitive will be the reading device 40. Furthermore, the membrane strip 41 also may include a reference zone 43 at another location upon the membrane strip 41. The reference zone 43 may be placed over the light pathway 59 in order to obtain a reference reading or a calibration of the reading device 40. Then, in a second step, the detection zone 42 may be placed over the light pathway 59 to obtain the sample reading. A spring 52 is shown in cross section above the light-absorbing member 57, which fits just above the membrane strip 41. The light-absorbing member 57 is capable of absorbing light that may undesirably enter the receiving port 45 from outside. Furthermore, the light-absorbing member 57 is capable of absorbing light that may proceed through the light pathway 59, and be transmitted completely through the membrane strip 41. This prevents reflection downward of stray light, improving sensitivity.

One alternate embodiment of the invention is shown in FIG. 5. A light barrier structure 81 is provided, below an LCD display 74. The light, barrier structure is bounded from above by top plate 72, and from below by bottom plate 78. A reading device 65 is comprised of a housing 73 having a receiving port 64 bounded upon the top by a hood 66. The receiving port 64 consists in part of a channel 68 that runs vertically as shown in FIG. 5. A light transmissive region 69, (which in FIG. 5 happens to be a rectangular aperture) is located in the bottom of the channel 68. A first notch 70 and a second notch 71 are provided as locating points to receive a membrane strip having nub 77 which will be seen in FIG. 5*a*. Screws 67*a* and 67*b* hold the hood 66 down upon the top plate 72. The function of the hood 66 is to reduce the amount of ambient light that impacts near the aperture 69, increasing the sensitivity of the reading device 65, and improving the signal to noise ratio of results obtained. An on/off switch 75 is shown near the right side of the housing 73.

FIG. 5*a* is a basic schematic taken in cross section along lines 5*a*-5*a* of FIG. 5 showing the basic internal architecture of the reading device 65 employed in the invention. Screws 67*a-b* hold down a top plate 72 upon bottom plate 78, and also function to hold hood 66 to plate 72. In cross section, one can see a light-absorbing member 80 that is positioned above membrane strip 76. A nub 77 fits into first notch 70 to register the membrane strip 76 in the appropriate position to receive light 91 from a light emitting diode (LED) 90. The light 91 travels to the membrane strip 76, and then is reflected downward along light pathway 93 to a sensor 92. In some applications, the sensor 92 is a diode. A housing 73 is also seen, and may include other components that are not shown in FIG. 5*a*.

Figure 5B:
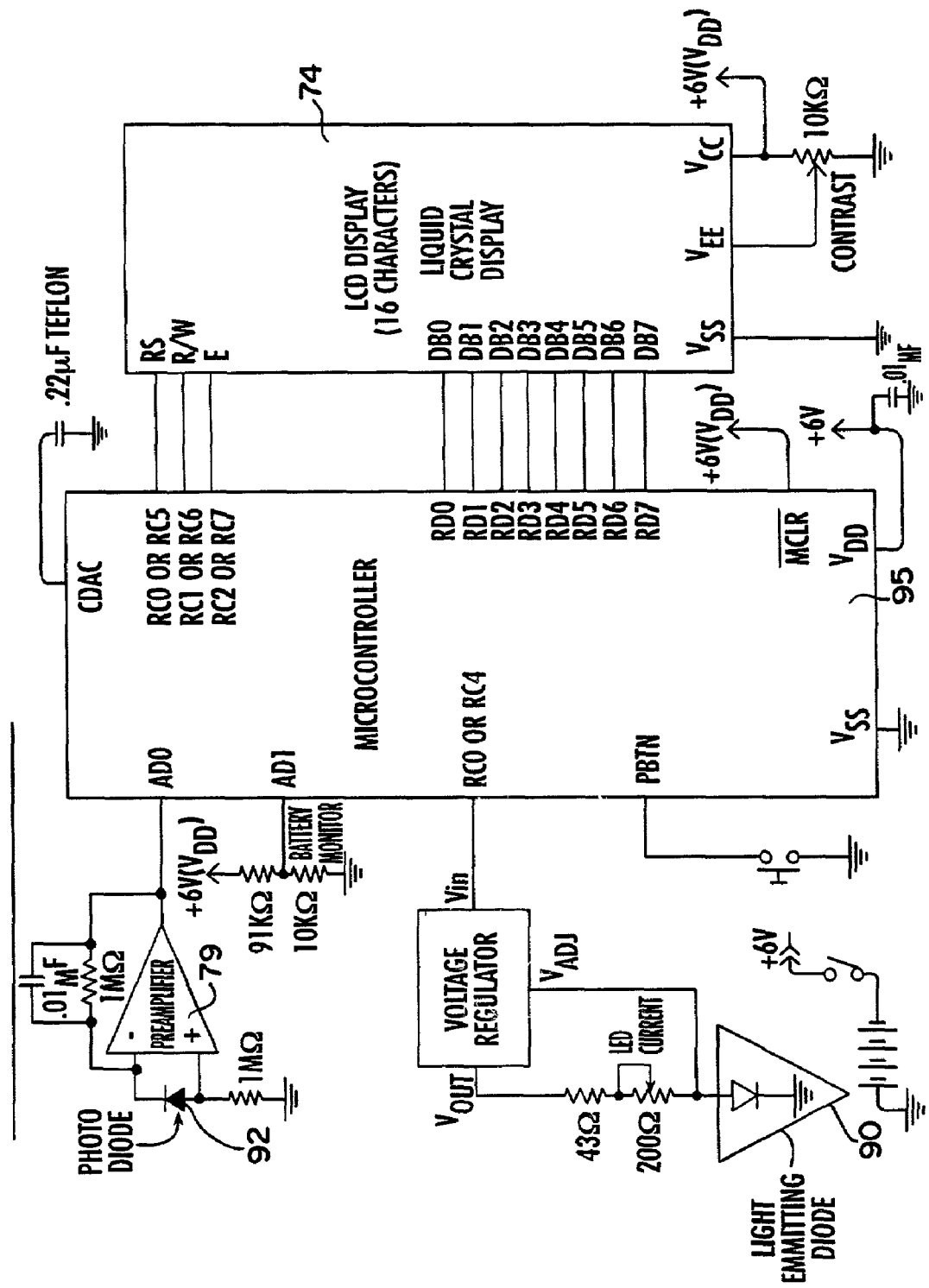

A basic schematic diagram of a reading device 65 is shown in FIG. 5*b*. In FIG. 5*b*, an LCD display 74 having 16 characters is shown on the right side of FIG. 5*b*. The LCD display 74 is connected to a micro controller 95. The microcontroller 95 directs the activities of the reading device 65, and regulates the light energy output of the light emitting diode (LED) 90, as shown in the lower left portion of FIG. 5*b*.

Likewise, a photo diode 92 receives light energy, and converts such energy to signals that are transmitted to a preamplifier 79, and then to the microcontroller 95. Eventually, the data output or result of an assay is illuminated on the LCD display 74, shown in FIG. 5.

The wavelength of the illumination radiation should be chosen to fall within the wavelength range over which the detector (photodiode) has appreciable responsivity (typically 400 nm to 1000 nm for a silicon photodiode. Furthermore, the wavelength of the illuminating radiation should be chosen to be near the maximal absorption wavelength of the detectable material used as the label in the lateral flow assay.

It is generally accepted that the detectable material used as a label or probe in the assay is one that will interact with light in the visible or near visible range, by absorption. For example, if the probe is a substance that appears blue to the naked eye when concentrated, the ideal electromagnetic radiation would likely be yellow. Particulate direct labels, including metallic and gold sols, non-metallic elemental sols (i.e. selenium or carbon) and colored latex (polystyrene) particles are suitable examples, as further described herein.

The source of light represented by the light emitting diode 90 may be comprised entirely of commercially available components. Suitable examples are commercially available LED's, preferably chosen to provide a suitable wavelength of light that is strongly absorbed by the detectable material concentrated in the detection zone 42. If desired, an array of LED's, which are energized in turn, could be used.

Figure 6:
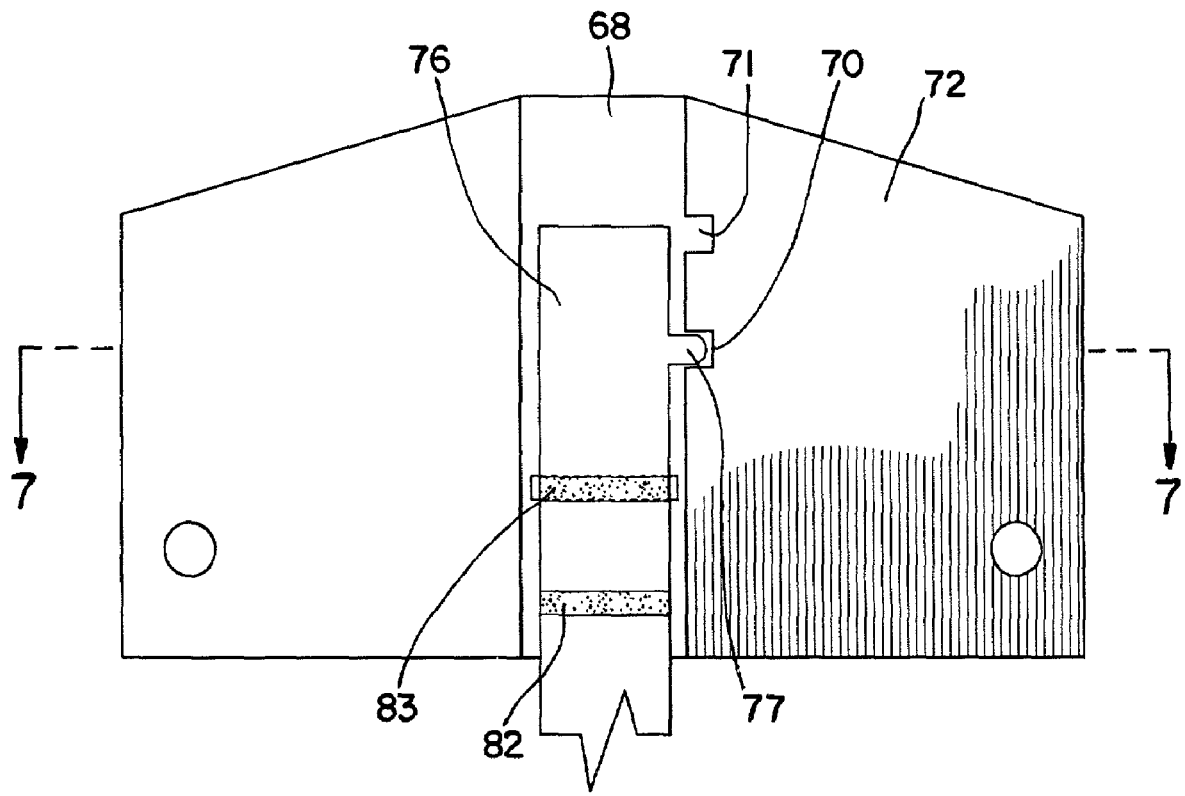
FIG. 6 shows a closer view of the membrane strip receiving portion of the embodiment previously shown in FIG. 5, showing one particular application in which the membrane strip includes a nub that interlocks into one or more notches.

FIG. 6 shows a more detailed view of the top plate 72 of one embodiment of the invention, which is seen in FIG. 5. A membrane strip 76 having a nub 77 is registered into first notch 70 as shown. In some embodiments of the invention, the nub 77 registers with the first notch 70 to take a reading from a reference zone 83 on the membrane strip 76. Then, once a reference or calibration reading is obtained, the membrane strip 76 may be lifted up and the position changed so that the nub 77 is integrated into the second notch 71. A detection zone 82 is shown on membrane strip 76. The detection zone 82 would then be placed over the aperture (aperture is not shown in FIG. 6) to obtain the test sample reading. The channel 68 into which the membrane strip 76 is placed is shown in FIG. 6.

Figure 7:
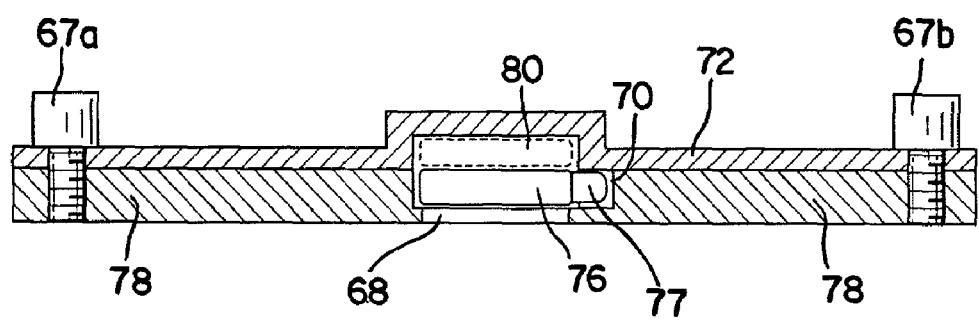
FIG. 7 shows a cross sectional view of the structure shown in FIG. 6, as taken along lines 7-7 in FIG. 6.

FIG. 7 shows a cross sectional view along lines 7-7 of FIG. 6. Screws 67*a-b* holds the hood 66, and a top plate 72 to a bottom plate 78. A membrane strip 76 is provided in the channel 68, so that the nub 77 is fitted into first notch 70. The light-absorbing member 80 is positioned over the membrane strip 76 in FIG. 7. The light-absorbing member 80 may include those materials described for component 57, including almost any type of material that is capable of absorbing light, such as a black or dark colored flocking, felt, plastic, metal, or other material.

The membrane-based device of the invention comprises several components, including a membrane, a sample pad, a conjugate pad and a wicking pad, or a combination of these items. The membrane typically includes at least two zones, that is, one or more detection zone(s) and one or more control or reference zone(s). A sample pad contacts one end of the conjugate pad.

One design of the assay device includes a liquid sample flow direction having a sample pad, conjugate pad, detection zone, and a pad, typically provided in that order from one end to the other end. In general, the wicking pad assists in promoting capillary action and fluid flow one-way through the membrane strip. The pad "pulls" the liquid containing the analyte along the membrane from one end of the membrane to another end of the membrane.

Probes used in the invention may comprise beads or particles. Such beads or particles may be comprised of latex, or other suitable material, as further described herein. In some applications, plain particles are used, while other applications may employ particles with capture reagents and/or antibodies conjugated upon the outer surface of the particle. The particles are typically colored with a dye that is visible to the eye, or to a detection apparatus. In other embodiments, the particles may include light absorbing materials such as metal sols, gold, or silver particles. Gold nanoparticles have been found to be suitable in some applications.

In one application of the invention a system for conducting a lateral flow assay is provided to detect the quantity of analyte that resides in a test liquid. The system comprises employing a probe analyte conjugate complex that is capable of generating a detectable signal. Furthermore, a membrane strip is provided and configured for mobilizing a test liquid which contains both a probe and an analyte conjugate. The membrane strip comprises a detection zone, in which the detection zone has deposited thereon a first capture reagent. The first capture reagent is immobilized upon the detection zone, and is configured for attaching to probe analyte conjugates to immobilize the probe analyte conjugates, thereby forming a sandwich complex within the detection zone.

A detection line may contain an immobilized second capture reagent (i.e.: antibody or other conjugating species), which serves to immobilize the unbound probes by binding to form a control probe complex (i.e.: immobile species) on a capture line. When significant numbers of the probe are immobilized in this way, a visibly distinctive line appears at one or more detection lines on the membrane strip. The control line may be embedded with a predetermined amount of second capture reagent.

In some instances, a comparison is made between the intensity levels of the calibration or control lines (or zone), or some other reference standard, and the detection line of the membrane strip, to calculate the amount of analyte present in a sample. This comparison step is accomplished with the reading device further described herein.

The membrane strip employed in the assay may be a cellulose ester, with nitrocellulose usually providing good results, but the invention is not limited to such compositions for the membrane strip.

It is to be understood that the invention can be configured for detecting a broad range of analytes, including therapeutic drugs, drugs of abuse, hormones, vitamins, glucose proteins (including antibodies of all classes), peptides, steroids, bacteria or bacterial infection, fungi, viruses, parasites, components or products of bacteria, allergens of all types, antigens of all types, products or components of normal or malignant cells, and the like.

The following analytes are examples of analytes that may be tested using the present invention: $T_4$, $T_3$, digoxin, hCG, insulin, theophylline, luteinizing hormone, organisms causing or associated with various disease states, such as streptococcus pyogenes (group A), Herpes Simplex I and II, cytomegalovirus, chlamydiae, and others known in the art.

U.S. Pat. No. 4,366,241 (Tom et al.) lists at columns 19-26 a variety of potential analytes of interest that are members of an immunologic pair, including proteins, blood clotting factors, hormones, microorganisms, pharmaceutical agents, and vitamins. Any of these analytes are suitable for use as the analyte in present invention.

Other examples of preferred ligands or analytes that may be detected include the following: human bone alkaline phosphatase antigen (HBAPAg); human chorionic gonadotropin (hCG); human luteinizing hormone (hLH); human follicle stimulating hormone (hFSH); creatine phosphokinase MB isoenzyme; ferritin; carcinoembryonic antigen (CEA); prostate specific antigen (PSA); CA-549 (a breast cancer antigen); hepatitis B surface antigen (HBsAg); hepatitis B surface antibody (HBsAb); hepatitis B core antigen (HBcAg); hepatitis B core antibody (HBcAb); hepatitis A virus antibody; an antigen of human immunodeficiency virus HIV I, such as gp120, p66, p41, p31, p24 or p17; the p41 antigen of HIV II; and the respective antiligand (preferably a monoclonal antibody) to any one of the above ligands. The HIV antigens are described more fully in U.S. Pat. No. 5,120,662 and in Gelderblood et al., Virology 156: 171-176 1987, both of which are incorporated herein by reference.

As used herein, the term "probe" refers generally to a structure that is capable of carrying an analyte in a lateral flow assay to a detection area or zone, which may or may not be in the form of a particle or microparticle. Furthermore, as used herein the term "probe-conjugate" refers to a species that is capable of carrying an analyte in a lateral flow assay to form a probe-conjugate complex, which binds a first capture reagent in a detection zone of a membrane strip to become a "sandwich complex" in the detection zone.

As used herein, the term "microparticle" is a more specific reference to a particular type of probe, and may include any beads or probes to which an antibody may be bound, whether covalently, or non-covalently such as by adsorption. An additional requirement for some particles that are used in a quantitative assay is that the particle contributes a signal, usually light absorption, which would cause the zone in which the particles were located to have a different signal than the rest of the membrane.

Optionally, metallic particles or metal could be used as the probe in the invention. These particles are commercially available as microspheres of substantially uniform diameter from companies such as British Biocell International, of Cardiff, United Kingdom.

By the phrase "membrane" or "membrane strip" as used herein is meant a test device or strip that employs a membrane and one or more reagents to detect the concentration of an analyte of interest in a test solution, preferably an aqueous test solution. At least one of the reagents associated with the membrane device is a binding partner of the analyte of interest.

Latex microparticles for use in the present invention are commercially available as polymeric microspheres of substantially uniform diameter (hereinafter "polymeric microspheres"), such as from Bangs Laboratories of Carmel, Ind., or Dow Chemical Co. of Midland, Mich. Although any polymeric microsphere that is capable of adsorbing or of being covalently bound to a binding partner may be used in the present invention, the polymeric microspheres typically are composed of one or more members of the group consisting of polystyrene, butadiene styrenes, styreneacrylic-vinyl terpolymer, polymethylmethacrylate, polyethylmethacrylate, styrene-maleic anhydride copolymer, polyvinyl acetate, polyvinylpyridine, polydivinylbenzene, polybutyleneterephthalate, acrylonitrile, vinylchloride-acrylates and the like or an aldehyde, carboxyl, amino, hydroxyl, or hydrazide derivative thereof.

The underivatized polymeric microspheres, such as polystyrene, are hydrophobic and passively adsorb other hydrophobic molecules, including most proteins and antibodies. Techniques for adsorbing a protein or polypeptide on a hydrophobic particle are provided in the publication by Cantarero, et al. "The Absorption Characteristics of Proteins for Polystyrene and Their Significance in Solid Phase Immunoassays," Analytical Biochemistry 105, 375-382 (1980); and Bangs, "Latex Immunoassays," J. Clin. Immunoassay, 13 127-131 (1980) both of which are incorporated herein by reference.

Various procedures for adsorbing molecules on polymeric microspheres are also described, in general terms, in Bangs, L. B., "Uniform Latex Particles," presented at a workshop at the 41st National Meeting, Amer. Assoc. Clin. Chem., 1989, and available in printed form from Seragen Diagnostics Inc., Indianapolis, Ind.; or Galloway, R. J., "Development of Microparticle Tests and Immunoassays," i.e., Seradyn Inc. of Indiana which is incorporated herein by reference.

The test solution may be a component of a biological fluid, such as extracted, diluted, or concentrated from a plant or animal, preferably a mammal, more preferably a human. Especially preferred biological fluids are serum, plasma, urine, ascites fluid, peritoneal fluid, amniotic fluid, synovial fluid, cerebrospinal fluid and the like, or a concentrate or dilution thereof.

In the practice of the invention, calibration and sample testing may be conducted under essentially exactly the same conditions at the same time, thus providing highly reliable quantitative results, and increased sensitivity.

The invention also may be employed for semi-quantitative detection. As the multiple control lines provide a range of signal intensities, the signal intensity of the detection line can be compared (i.e. such as for example, visually) with the control lines. Based on the intensity range the detection line falls, the possible concentration range for the analyte may be determined. The probes may be latex beads labeled with any signal generating species or the labeled latex beads further conjugated with antibodies.

It is understood by one of ordinary skill in the art that the present discussion is a description of exemplary embodiments only, and is not intended as limiting the broader aspects of the present invention, which broader aspects are embodied in the exemplary constructions. The invention is shown by example in the appended claims.

What is claimed is:

1. A system for conducting a lateral flow assay to detect the presence or quantity of an analyte in a sample, the system comprising:
    (a) a lateral flow membrane strip comprising a detection zone, wherein upon application, the sample is capable of traversing through the membrane strip to the detection zone; and
    (b) a reading device comprising:
        (i) a housing within which is contained an electromagnetic radiation source and a sensor capable of detecting the intensity of electromagnetic radiation, wherein the electromagnetic radiation source and sensor are positioned so that electromagnetic radiation emitted from the source is capable of being reflected from the lateral flow membrane strip to the sensor, the housing having an exterior surface;
        (ii) a light barrier structure comprising a top plate and a bottom plate, the bottom plate being positioned adjacent to the exterior surface of the housing, wherein a receiving port is defined between the top plate and the bottom plate, the lateral flow membrane strip being capable of insertion into the receiving port, wherein the bottom plate defines an aperture through which electromagnetic radiation from the source is capable of passing before contacting the lateral flow membrane strip, the aperture having a size that approximates the size of the detection zone; and
        (iii) a light absorbing member positioned within the receiving port to absorb stray light, the light absorbing member comprising an absorption pad that is located adjacent to the membrane strip upon insertion into the receiving port, the absorption pad covering an area under which the membrane strip is impacted by electromagnetic radiation.

2. The system of claim 1, further comprising a pressure plate that is positioned in the receiving port between the top plate and the bottom plate for bearing against the lateral flow membrane strip upon insertion.

3. The system of claim 2, wherein the pressure plate is spring loaded.

4. The system of claim 1, wherein the light-absorbing member comprises a flexible material.

5. The system of claim 1, wherein the receiving port defines a first stop position for a reference reading and a second stop position for a sample reading.

6. The system of claim 5, wherein one or more of the stop positions is formed by notches in the bottom plate.

7. The system of claim 1, wherein a capture reagent is immobilized within the detection zone, the capture reagent being configured to directly or indirectly bind to the analyte.

8. The system of claim 1, wherein the aperture is elongated.

9. The system of claim 1, wherein the aperture is circular.

10. The system of claim 1, wherein the area of the aperture is 1.8 times or less than the area of the detection zone.

11. The system of claim 1, wherein the area of the aperture is 1.3 times or less than the area of the detection zone.

12. The system of claim 1, wherein the electromagnetic radiation source comprises a light emitting diode.

13. The system of claim 1, wherein the sensor comprises a photodiode.

14. The system of claim 1, further comprising a display for providing results of the assay.

15. The system of claim 1, further comprising a sample pad in fluid communication with the membrane strip, the sample pad defining the point of application for the sample.

16. The system of claim 1, further comprising a wicking pad in fluid communication with the membrane strip.

* * * * *